United States Patent [19]

Klapper et al.

[11] Patent Number: 5,019,083

[45] Date of Patent: May 28, 1991

[54] IMPLANTING AND REMOVAL OF ORTHOPEDIC PROSTHESES

[75] Inventors: Robert C. Klapper, Los Angeles; James T. Caillouette, Newport Beach, both of Calif.

[73] Assignee: Advanced Osseous Technologies, Inc., Aliso Viejo, Calif.

[21] Appl. No.: 304,820

[22] Filed: Jan. 31, 1989

[51] Int. Cl.$^5$ ............................................ A61B 17/56
[52] U.S. Cl. ........................................ 606/99; 606/86
[58] Field of Search ............. 128/92 V, 92 VT, 92 R, 128/92 VP, 92 VZ; 606/53, 86, 99; 623/22, 23

[56] References Cited

U.S. PATENT DOCUMENTS

| | | | |
|---|---|---|---|
| 2,714,890 | 8/1955 | Vang | 128/305 |
| 3,076,904 | 2/1963 | Kleesattel et al. | 310/26 |
| 3,823,717 | 7/1974 | Pohlman et al. | 128/305 |
| 4,188,952 | 2/1980 | Loschilov et al. | 128/305 |
| 4,248,232 | 2/1981 | Engelbrecht et al. | 128/305 |
| 4,298,074 | 11/1981 | Mattchen | 173/129 |
| 4,425,115 | 1/1984 | Wuchinich | 604/22 |
| 4,636,219 | 1/1987 | Pratt et al. | 623/22 |
| 4,778,469 | 10/1988 | Lin et al. | 623/23 |
| 4,828,566 | 5/1989 | Griss | 623/23 |
| 4,832,683 | 5/1989 | Idemoto et al. | 606/79 X |

FOREIGN PATENT DOCUMENTS

| | | | |
|---|---|---|---|
| 121491 | 10/1984 | European Pat. Off. | 623/22 |
| 243298 | 10/1987 | European Pat. Off. | 623/23 |
| 2614524 | 11/1988 | France | 623/23 |
| 1371335 | 10/1974 | United Kingdom | 623/23 |

OTHER PUBLICATIONS

DePuy Fracture Appliances, 1964.
Richards Manf., Orthopedic Catalog, pp. 10, 14, 20, 1981.
Cameron, H. U., Contemporary Orthopaedics 18(5): 565-572 (1989).
Zhou, X. M. et al., J. Arthroplasty 5 (1): 71-82 (1990).
Schwartz, Jr., J. T. et al., J. Bone & Joint Surgery 71-A(8):1135-1142 (1989).
Harris et al., J. Bone & Joint Surgery 63-A(5):843-5 (Jun. 1981).
Karpman et al., Osteopadic Review XVI(1):84-4 (Jan. 1987).
Lin, Clin. Orthopaedics & Related Rsch. 193:90-102 (Mar. 1985).
McClelland et al., Orthopaeedic Review XV(6): 75-80 (Jun. 1986).
Moreland et al., Clin. Orthopaedics & Related Rsch. 212:245-9 (Nov. 1986).
Weis, Orthopedic Clinics of N. Amer. 8(1):43-5 (Jan. 1977).

*Primary Examiner*—Robert A. Hafer
*Assistant Examiner*—Kevin G. Rooney
*Attorney, Agent, or Firm*—Knobbe, Martens, Olson & Bear

[57] ABSTRACT

A hip joint prosthesis or the like may be removed from the bone for a revision by applying ultrasonic vibration sufficient to disrupt connection of the prosthesis with the bone. This is particularly desirable for disrupting cancellous bone at the interface adjacent to the porous surface of a prosthesis designed for ingrowth of cancellous bone. Preferably the ultrasonic vibrations are applied to the prosthesis with sufficient energy for disrupting cancellous bone at the porous surface interface or softening a cement employed for securing the prosthesis to the bone. An ultrasonically vibrated osteotome may be inserted along the porous surface of a prosthesis for disrupting cancellous bone adjacent to the interface. Preferably the ultrasonic transducer is coupled to the prosthesis by a self-holding taper on the prosthesis and a complementary tapered socket connected to an ultrasonic transducer. Ultrasonic vibrations may also be employed for forming a cavity into which a prosthesis is implanted. This technique includes vibrating the prosthesis itself as it is inserted to enlarge the cavity and assure a tight fit.

7 Claims, 2 Drawing Sheets

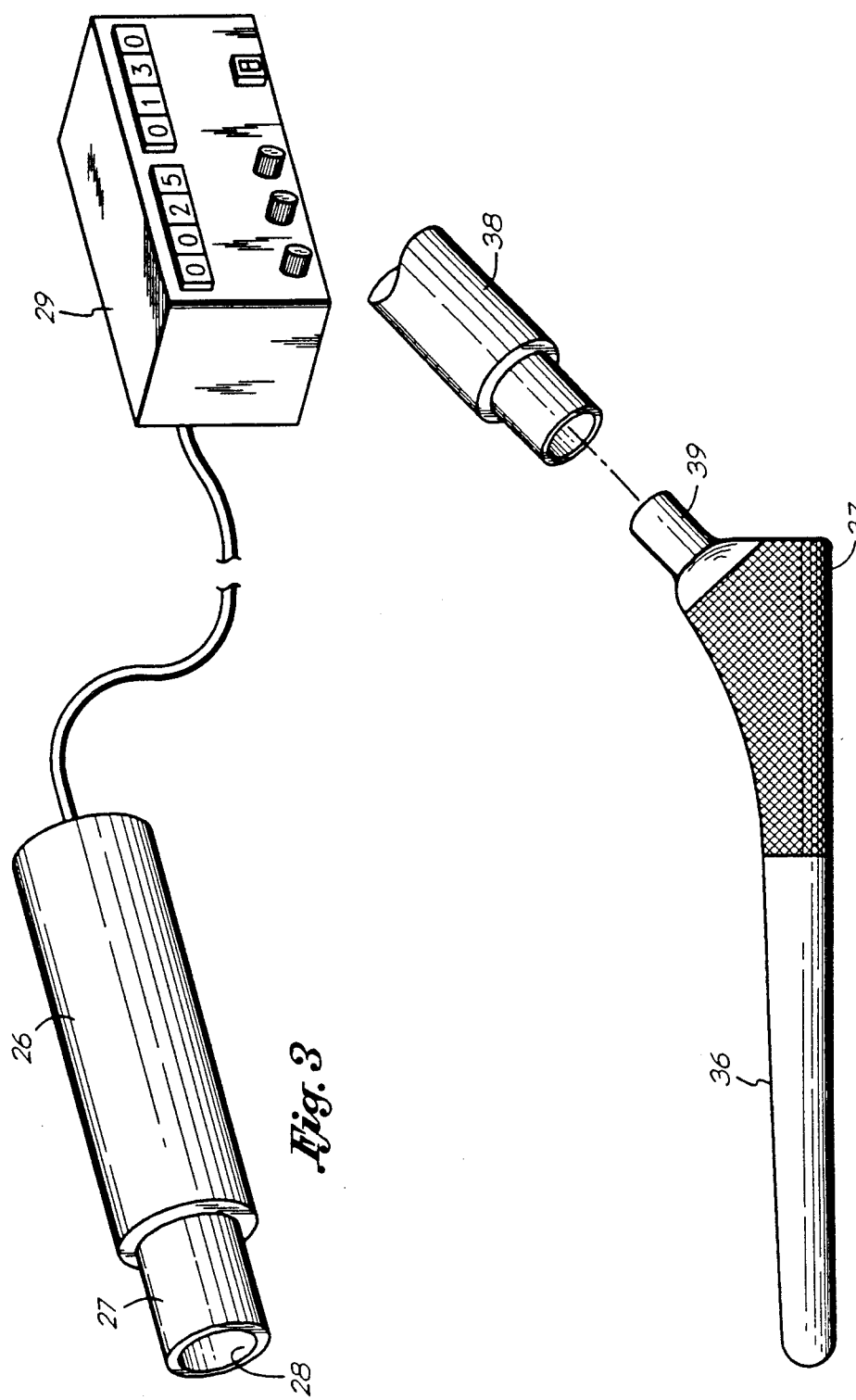

IMPLANTING AND REMOVAL OF ORTHOPEDIC PROSTHESES

FIELD OF THE INVENTION

This invention relates to techniques and apparatus for introducing and removing an orthopedic prosthesis such as a femoral component of a hip joint replacement, acetabular cup, knee joint, shoulder joint, or the like.

BACKGROUND OF THE INVENTION

It has been over sixty years since the first use of replacement parts for hip joints. There have been many advances in the prosthetic components, materials, surgical techniques and the like, so that total hip joint replacement has become relatively commonplace. Related techniques have been also been used for replacing knee and shoulder joints.

There are two principal components to a hip replacement prosthesis. One is an acetabular cup which is implanted in the acetabulum. The acetabular cup provides a spherical socket which is the bearing surface for the replacement joint. The other component comprises a femoral stem which is fitted into the medullary canal of the femur and a femoral head on the stem having a spherical surface which meets with the acetabular socket.

The femoral portion of the prosthesis is inserted by cutting off the femoral neck with or without removing the greater trochanter. The medullary canal is then prepared using drills, reamers and successively larger rasps to produce a cavity which is closely complementary to the femoral stem. After cleaning, the femoral stem is driven into place in the canal with what is essentially a press fit. Preparing the cavity to fit the stem is tedious and prolongs the period the patient must be kept under anaesthesia.

The femoral stem may be held in place by a polymethylmethacrylate cement (PMMA) or it may be provided with a porous surface on the shank which accommodates ingrowth of cancellous bone which secures the femoral component in the femur.

The acetabular cup is implanted after grinding a socket in the pelvis to receive it. The socket may be secured with cement, or may be fastened to the bone with screws after a press fit. Similar techniques, differing in detail are used for implanting replacement shoulder joints, knees and the like.

Despite advances in the technology of hip replacement, it is found that a substantial number of "revisions" are required. Such revisions involve removing components of the hip joint and replacing them. Such revisions may be required shortly after the original surgery due to complications. More commonly they occur eight or ten years after the original surgery due to any of a number of problems that may arise. Such revisions are traumatic for the patient, tedious for the surgeon, and quite time consuming for surgical staff and facilities.

A principal problem in revisions is removal of the femoral component. Some such components are made with transverse holes or threaded holes for connection of tools to extract the femoral stem from the medullary canal. Repeated hammer blows may be applied for driving the stem out of the cavity. Sometimes a window is cut in the femoral cortex near the distal end of the shank, and a punch and hammer are used for driving the shank toward the open end of the femur. Trauma to the patient can be severe and breakage of parts of the femur is not unusual. The techniques employed for removing the femoral component have been characterized as barbaric.

Another technique that has been attempted is removal of the polymethylmethacrylate with an ultrasonically vibrated osteotome. Such a technique is described in U.S. Pat. No. 4,248,232 by Engelbrecht. The osteotome is used for scooping out polymethylmethacrylate cement softened by the ultrasonic vibrations.

Other techniques involve use of long, thin osteotomes for cutting either the cement used for securing the prosthesis in the medullary canal or cancellous bone in the case of an ingrowth prosthesis. In effect, the osteotomes are long chisels which are tapped to disintegrate the cancellous bone or cement and free the prosthesis from the surrounding cortex. For example, in a paper entitled "Atraumatic Removal of a Well-Fixed Porous Ingrowth Hip Prosthesis", *Orthooedic Review*, Vol. 15, No. 6, June 1986, page 387, Doctors McClelland, James and Simmons describe removal of a femoral component "by the use of an oscillating saw and long, thin osteotomes to carefully separate the prosthesis from its intra-medullary environment. This portion of the procedure was both tedious and somewhat time-consuming, but no iatrogenic damage to the cortical tube of the proximal femur resulted. After the proximal half of the prosthesis had been freed up in this manner, the prosthesis was then extractable, using multiple heavy hammer blows applied to vise grips attached to the end of a McReynolds-wedge extractor."

It is clear that faster and less traumatic techniques are desirable for removing components of prostheses inserted in the medullar canal. It is also desirable to provide quicker and easier techniques for implanting prostheses.

SUMMARY OF THE INVENTION

There is, therefore, provided in practice of this invention according to a presently preferred embodiment improved techniques for removing a joint prosthesis comprising a removable femoral head connected to the body of the prosthesis by coupling an ultrasonic transducer directly to the prosthesis and applying a sufficient ultrasonic signal for vibrating the prosthesis and loosening it from connection with bone. Such a technique may be used with either a cemented prosthesis or a cementless ingrowth prosthesis. The ultrasonic vibrations may either soften cement holding the prosthesis in place or disrupt cancellous bone adjacent to the porous surface of that type of prosthesis.

Alternatively, one may couple an ultrasonic transducer to an osteotome and insert the osteotome through cancellous bone adjacent to the porous surface of a prosthesis for ultrasonically disrupting the cancellous bone.

The cavity for receiving an orthopedic prosthesis may be shaped to receive the prosthesis tightly by employing ultrasonically vibrated tools shaped similarly to the prosthesis. Preferably, the prosthesis itself is used as a "tool" to finally shape the cavity as it is pressed into place, thereby assuring a tight fit. Small rasp-like teeth may be provided on surfaces of the prosthesis to aid in implanting while being ultrasonically vibrated.

The technique is practiced with an ultrasonic transducer connected to a power supply for generating ultrasonic vibrations. These ultrasonic vibrations may be coupled to the joint prosthesis by any of a variety of means such as a threaded connection or a socket on the transducer connectable to a self-holding taper on such a prosthesis.

BRIEF DESCRIPTION OF THE DRAWINGS

These and other features and advantages of the invention will be appreciated as the same becomes better understood by reference to the following detailed description when considered in connection with the accompanying drawings wherein:

FIG. 3 is a schematic view of an ultrasonic transducer for coupling to a femoral component as illustrated in FIG. 2;

FIG. 4 is a side view of a femoral component including rasp-like teeth.

DETAILED DESCRIPTION

Figures 1, 2:
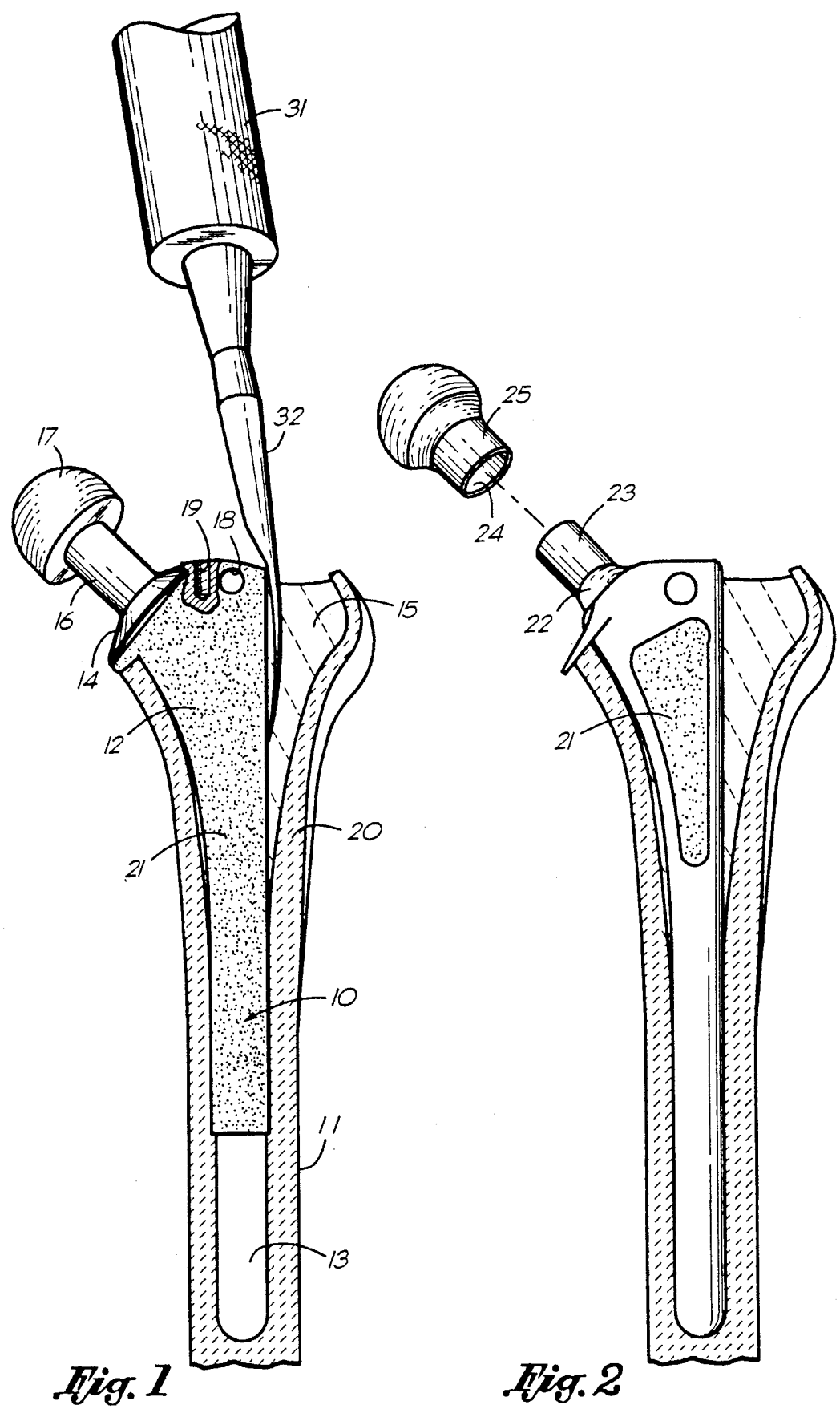
FIG. 1 is a side view partly in cross section of an exemplary femoral implant component of a hip replacement joint as implanted in a femur with an osteotome for disrupting cancellous bone.
FIG. 2 is a side view of another embodiment of femoral component of a hip replacement joint implanted in a femur, with the head of the component exploded from the body.

FIG. 1 illustrates an exemplary femoral component 10 of a hip prosthesis joint implanted in the end of a femur which has the trochanter osteotomized. The body 12 of the prosthesis and at least a portion of the shank 13 which extends along the medullary canal have a porous surface. Such a porous surface is provided on the prosthesis by some manufacturers in the form of metal beads having the same composition as the prosthesis which are sintered onto the solid metal of the prosthesis. Other manufacturers employ a mat of metal wires sintered onto the surface. In either type, the porous surface portion provides a substrate into which growth of cancellous bone 15 may occur for rigidly securing the prosthesis to the femur. Some prostheses have a collar 14 which bears against the cortex 20 at the end of the femur. Collarless prostheses are also used.

A neck 16 connects a ball or head 17 to the body of the prosthesis. The spherical head provides the bearing engagement with the acetabular cup (not shown) secured to the patient's pelvis.

A transverse hole 18 extends through the prosthesis for engagement by a tool for extracting the prosthesis from the femur in the event a revision is required. In addition or alternatively, a threaded hole 19 is provided in the end of the body for receiving a tool which can provide a longitudinal force for withdrawing or inserting the prosthesis.

Another type of prosthesis as illustrated in FIG. 2 has a porous surface area 21 on the body for receiving ingrowth of cancellous bone for securing the prosthesis in the medullary canal. In the illustrated embodiment the neck 22 of the prosthesis has a self-holding taper 23 at its proximal end for receiving a complementary female taper 24 in a head 25 which can thereby be removably secured to the prosthesis. A variety of self-holding tapers with different angles of taper and standard dimensions may be used. These include the Morse, Brown and Sharpe, Jarno, Sellers, Reed, American Standard and Metric tapers. Taper angles of 5% or less are customary. Self-holding tapers cause the shank, when seated firmly in the socket, to tend to stay in place by friction due to the small taper angle. For example, when the head is driven onto a Morse-type taper with a couple of mallet blows, it cannot be removed manually. A larger longitudinal force may be used for separating a self-holding taper. A removable head for a prosthesis provides the opportunity for stocking heads with varying lengths of neck for fitting to a variety of standard bodies for mixing and matching to fit the prosthesis to an individual patient. For example, up to ten different dimensions of body may be matched with a dozen or so different heads with varying diameters and neck lengths.

For removing a prosthesis implanted in a femur, an ultrasonic transducer 26 (FIG. 3) is coupled to the prosthesis. At the end of the transducer there is a metal sleeve 27 having a socket 28 with a female self-holding taper matching the taper on the neck of the prosthesis. The intimate engagement of the self-holding taper provides high efficiency coupling of the ultrasonic vibrations from the transducer to the prosthesis.

The ultrasonic transducer may be any of a variety of known transducers. These may include electrostrictive, magnetostrictive or electromagnetic devices, as may be preferred by the equipment manufacturer. Each of these has certain advantages depending on the frequency range, amplitude of vibration, and power level.

The ultrasonic transducer is driven by an ultrasonic signal from a conventional power supply 29. Such power supplies typically permit the user to determine the frequency of oscillation and the power level of the ultrasonic signal sent to the transducer. For purposes of disrupting cancellous bone ingrown into the porous surface of a joint prosthesis, a frequency corresponding to a resonant frequency of the prosthesis is desirable for maximizing amplitude of vibration with a given signal strength. Some tuning of frequency for a particular prostheses implanted in bone may be employed in lieu of merely increasing signal strength. It is desirable to employ a frequency in the range of from about 20,000 to 40,000 Hertz, preferably around 25,000 Hertz.

For removing the prosthesis, the transducer is coupled to the self-holding taper on the prosthesis and the prosthesis is ultrasonically vibrated by applying a signal to the transducer. The vibration of the prosthesis disrupts cancellous bone at the surface of the prosthesis due to the impedance mismatch between the metallic prosthesis and the cancellous bone surrounding it. There is a substantial impedance mismatch between the portion of the prosthesis which does not have a porous surface and the surrounding cancellous bone, such as along the length of the shank, and the bone at the interface is readily disrupted. There is less of an impedance mismatch and also less energy transfer at the interface between the porous metal surface and the bony ingrowth. A somewhat higher energy input level is therefore required for disrupting cancellous bone adjacent to the surface of the porous ingrowth area.

After applying ultrasonic vibrations for several seconds, an attempt is made to withdraw the prosthesis. If the transducer is in the way, it may be removed before trying to withdraw the prosthesis to avoid damaging the transducer. In the event the prosthesis is not readily removed by application of pressure or moderate impact, the ultrasonic signal strength can be increased to try again to see if there has been adequate disruption of the cancellous bone at the interface with the porous surface.

Alternatively, the disruption of cancellous bone by the ultrasonic vibrations may be investigated by probing with a thin instrument passed along the body adjacent to the porous surface before an attempt is made to withdraw the prosthesis.

Some prostheses, such as the one illustrated in FIG. 1, have a head integral with the body rather than being connected thereto by a self-holding taper. The ultrasonic transducer may be coupled to such a prosthesis by way of threaded hole, or a spherical socket may be used to mate with the spherical head and provide good energy transfer.

An alternative technique may be employed for disrupting cancellous bone adjacent to the porous surface of the prosthesis. According to this technique an ultrasonic transducer 31 (FIG. 1) is threaded onto a conventional osteotome 32 and the osteotome is inserted along the porous ingrowth surface of the prosthesis 10 for disrupting a narrow channel of cancellous bone. By repeatedly inserting ultrasonically vibrating osteotomes along different areas of the body of the prosthesis, sufficient cancellous bone can be disrupted to free the prosthesis from the bone and permit its withdrawal with limited trauma to the patient. This technique for disrupting cancellous bone may be used in areas readily accessible at the proximal end of the prosthesis and ultrasonic vibration of the entire prosthesis may be employed for disrupting cancellous bone adjacent to the distal end of the prosthesis.

It should be noted that disruption of the bone occurs at the impedance mismatch between the metal and the bone. There is sufficiently low energy transfer through the bone and other tissues to avoid significant damage to the cancellous bone or cortex remote from the interface. Preferably the energy level is kept low enough that there is insignificant disruption of cortical bone in places where the shank of the prosthesis contacts such bone.

When removing a porous ingrowth prosthesis by ultrasonically vibrating osteotomes, equipment similar to that described in the Engelbrecht patent may be employed. Osteotome blades are available with male threaded ends for attachment to handles or the like. The threaded end makes a convenient place for coupling an ultrasonic transducer to the osteotome. The threaded tip of a transducer may be placed in the threaded hole 19 in a prosthesis as illustrated in FIG. 1 for efficiently coupling the ultrasonic vibrations between the transducer and the prosthesis. The way of coupling the transducer to the osteotome is not of significance and other means may be employed. Coupling to the self holding taper of a prosthesis is preferred.

It will also be noted that the power levels required when a transducer is coupled to an osteotome are considerably less than when a transducer is coupled to the prosthesis itself, since the area of the interface at which cancellous bone is being disrupted is considerably different.

A technique for removing a prosthesis by ultrasonically vibrating it may also be employed where the prosthesis has a substantially smooth surface and is secured in the bone by a cement such as polymethylmethacrylate. In such an embodiment the PMMA remains softened and can be readily disrupted while ultrasonic vibrations are being applied. When vibrations are discontinued, the PMMA may become more rigid. It is, therefore, desirable when removing a prosthesis which is cemented in place, to apply ultrasonic vibrations and a withdrawing force simultaneously. This assures that a minimum withdrawal force is used for withdrawing the component. Again, if the prosthesis is not removed readily with a withdrawing force which may be steady or in the form of impact, the power level may be increased until a reasonable withdrawing force is sufficient for withdrawing the prosthesis from the medullary canal.

An ultrasonic technique may also be employed for implanting an original or a replacement prosthesis during revision surgery. The preparation of a cavity in which a prosthesis is placed can be tedious and careful shaping of the cavity is important so that a tight fit is obtained. This is particularly significant for implantation of prostheses having porous surfaces for ingrowth of cancellous bone. At present such a cavity is formed by drilling and reaming to form a cavity of roughly the right shape and size and then finishing the cavity with a rasp or series of rasps complementary to the shape of the prosthesis, which are hammered or pressed into the medullary canal.

In practice of this invention at least the final reaming of the cavity is done by ultrasonically vibrating an object having the same shape as the prosthesis, with sufficient energy to disrupt cancellous bone, and pressing the ultrasonically vibrating object into the cancellous bone for forming a cavity complementary to the prosthesis. Preferably the object has rasp-like teeth which further aid in disrupting cancellous bone so that the object can be pressed into the cavity without excessive force which could fracture the cortex.

The object employed for forming a cavity in the cancellous bone complementary to the prosthesis may be a rasp that is inserted and temporarily left in place for testing and other procedures before the prosthesis is implanted. Preferably the object comprises the prosthesis itself. Thus, as illustrated in FIG. 4, a prosthesis 36 such as the femoral component of a hip joint has a plurality of rasp-like teeth on surface areas 37 on at least the tapering body portion of the prosthesis. An exemplary size for the rasp-like teeth is about 400 micrometers peak-to-peak. An ultrasonic transducer 38 is coupled to the self-holding taper 39 on the neck of the prosthesis as hereinabove described. As the prosthesis is ultrasonically vibrated by the transducer, it is pressed into the cavity and the teeth cut cancellous bone until the prosthesis fits tightly in the cavity. The transducer can then be removed and the prosthesis left in the cavity so formed.

It is not important that the swarf produced by the teeth on the prosthesis be removed from the cavity. On the contrary, it is not unusual to pack a portion of the cavity with fragments of cancellous bone and tissue removed in forming the cavity to assure a tight fit of the prosthesis. Such materials appear to promote growth of cancellous bone and may enhance fixation of a porous ingrowth prosthesis in the cavity. It is desirable to employ teeth with a spacing from about 50 to 400 micrometers since that is appropriate for ingrowth of cancellous bone. Thus, the newly grown cancellous bone between the teeth tends to secure the prosthesis in the cavity. In other words the teeth are analogous to the porous surface on conventional ingrowth type prostheses.

Although limited embodiments have been described and illustrated herein, it will be readily appreciated by those skilled in the art that there may be many modifications and variations of practice of this invention. For example, although coupling the ultrasonic transducer to the self-holding taper on a prosthesis is particularly desirable, any of a variety of coupling means may be employed. As should already be apparent from the description, these techniques may be employed in combination with other conventional techniques for loosening and removing a prosthesis from a joint.

Further, although described in the context of a hip joint replacement, it will be apparent that similar techniques may be used with implants of shoulder joints, knees and the like, or with pins used for reinforcing bone. For example, ultrasonic vibrations may be used for implanting the keel of the tibial component of a knee joint. Ultrasonic vibration of a rasping object may be used for final shaping of the cavity for an acetabular cup. It is, therefore, to be understood that within the scope of the appended claims, this invention may be practiced otherwise than as specifically described.

What is claimed is:

1. A method for removing a prosthesis having a porous surface ingrown with cancellous bone comprising the steps of:
   ultrasonically disrupting cancellous bone adjacent to at least the porous surface of the prosthesis; and
   withdrawing the prosthesis from the bone.

2. A method as recited in claim 1 wherein the disrupting step comprises applying ultrasonic vibration to the prosthesis by direct coupling to an ultrasonic transducer.

3. A method as recited in claim 2 wherein the ultrasonic vibration is applied simultaneously with a withdrawing force.

4. A method as recited in claim 2, wherein the ultrasonic vibration has a frequency corresponding to a resonant frequency of the prosthesis.

5. A method as recited in claim 2 wherein the ultrasonic transducer is vibrated with a frequency in the range of from 20,000 to 40,000 Hertz.

6. A method as recited in claim 1 wherein the disrupting step comprises coupling an ultrasonic transducer to an osteotome for vibrating the osteotome, and inserting the vibrating osteotome through cancellous bone adjacent to at least the porous surface.

7. A method as recited in claim 6 wherein the osteotome is vibrated with a frequency in the range of from 20,000 to 40,000 Hertz.

* * * * *